United States Patent [19]

Haber et al.

[11] Patent Number: 5,267,973

[45] Date of Patent: Dec. 7, 1993

[54] SAFETY SYRINGE WITH OFF-AXIS NEEDLE CANNULA

[75] Inventors: Terry M. Haber, Lake Forest; William H. Smedley, Lake Elsinore; Clark B. Foster, Laguna Niguel, all of

[73] Assignee: Habley Medical Technology Corporation, Laguna Hills, Calif.

[21] Appl. No.: 682,058

[22] Filed: Apr. 8, 1991

[51] Int. Cl.$^5$ .............................................. A61M 5/32
[52] U.S. Cl. .................................. 604/195; 604/110; 604/240; 128/765
[58] Field of Search ............... 604/110, 125, 181, 183, 604/187, 188, 192, 195, 198, 218, 263, 240; 128/919, 764, 765

[56] References Cited

U.S. PATENT DOCUMENTS

| | | | |
|---|---|---|---|
| 4,573,976 | 3/1986 | Sampson et al. | 604/263 |
| 4,834,717 | 5/1989 | Haber et al. | |
| 4,900,307 | 2/1990 | Kulli | 604/110 |
| 4,927,414 | 5/1990 | Kulli | 604/198 |
| 4,941,883 | 7/1990 | Venturini | 604/195 |
| 4,944,723 | 7/1990 | Haber et al. | |
| 4,966,593 | 10/1990 | Lennox | 604/198 |
| 5,013,301 | 5/1991 | Marotta, Jr. et al. | 604/218 |
| 5,052,403 | 10/1991 | Haber et al. | |
| 5,064,419 | 11/1991 | Gaarde | 128/919 |
| 5,085,640 | 2/1992 | Gibbs | 604/110 |
| 5,147,323 | 9/1992 | Haber et al. | 604/232 |

FOREIGN PATENT DOCUMENTS 0287950 10/1988 European Pat. Off. ............ 604/110

Primary Examiner—C. Fred Rosenbaum
Assistant Examiner—Ronald K. Stright, Jr.
Attorney, Agent, or Firm—Townsend and Townsend, Khourie and Crew

[57] ABSTRACT

A syringe (2), of the type having a barrel (4) with a plunger (6) disposed within the bore of the barrel, includes a needle assembly (22) housed within a needle assembly guide (14) positioned along the exterior (16) of the syringe barrel. The needle assembly guide provides a path along which the needle assembly moves, between an extended position, with the needle exposed, and a retracted position, with the needle encompassed by the needle guide. A flow path (36, 44) exists between the interior (46) of the syringe barrel and the needle assembly when the needle assembly is in the extended position. Additionally, the needle assembly can be irreversibly locked (54, 60) in the retracted position to prevent syringe reuse.

3 Claims, 4 Drawing Sheets

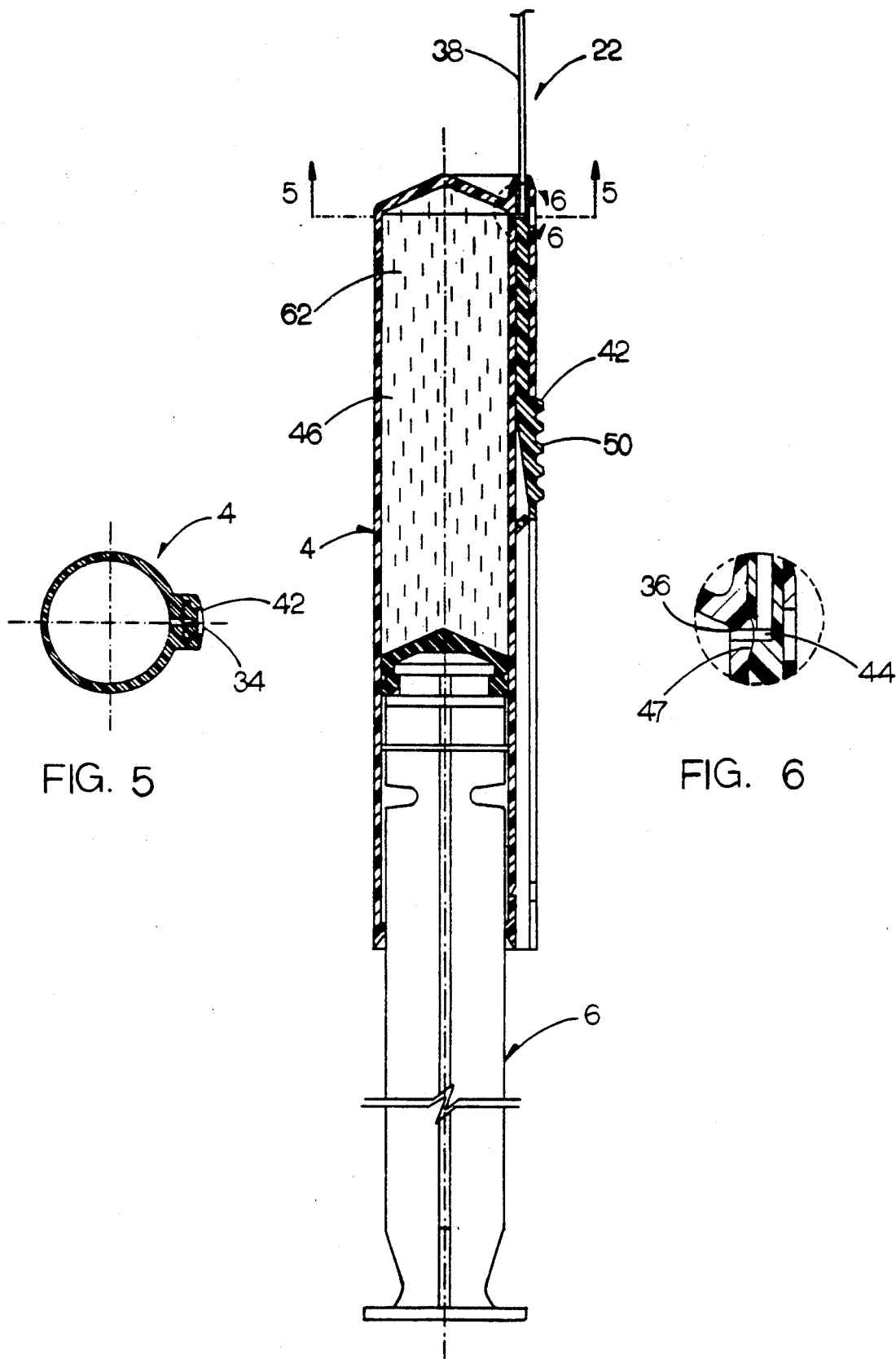

SAFETY SYRINGE WITH OFF-AXIS NEEDLE CANNULA

CROSS REFERENCE TO RELATED APPLICATION

This application is related to U.S. patent application Ser. No. 07/682,088, filed on the same date as this application, for PACKAGED PHARMACEUTICAL-TYPE SAFETY SYRINGE WITH OFF-AXIS NEEDLE CANNULA, the disclosure of which is incorporated by reference.

BACKGROUND OF THE INVENTION

Syringes are widely used for the administration of drugs or other substances to, or for the withdrawal of fluids from, a body. Syringes are also used for a variety of health industry and other purposes as well. Typically, a syringe includes a barrel and a plunger. The plunger is reciprocally disposed within the barrel, with the plunger protruding from the proximal end of the barrel throughout its range of movement. To utilize the syringe a needle will generally be attached to the distal end of the syringe barrel, the needle being coaxial with the central axis of the barrel. The syringe may be provided with the needle pre-placed in this location, with a protective cap or sheath covering the needle. Alternatively, and more commonly, a needle with an associated sheath is attached to the distal end of a syringe barrel prior to use.

Generally, the syringe barrel and needle sheath are mass produced from a low cost material, such as polypropylene, by a cost-efficient method such as injection molding. The needle is made of a suitable material, such as 304 stainless steel.

Subsequent to use the syringe needle will often be recapped and then discarded in a suitable disposal container. In some settings the needle may be clipped prior to recapping, in an effort to preclude any illicit use of the needle after its disposal; however, clipping can release toxic and/or infectious aerosolization mists.

For many applications a syringe with a coaxial needle will suffice. However, there are numerous situations in which this embodiment presents significant obstacles to the effective use of the syringe. The typical syringe with a coaxial needle may have limited use when administering fluids intravenously, or particularly subcutaneously. The foregoing problems are exacerbated when larger volumes of fluid, and consequently larger diameter syringe barrels are utilized.

Furthermore, very serious, even life threatening, problems may be associated with the attachment, but more particularly with the removal, of a needle from such a syringe. The problems associated with the recapping and disposal of previously-used syringe needles are also severe. In the medical industry an exceptionally high percentage of job-related needle sticks occur during the process of needle recapping. Such needle sticks may serve as a mode for the spread of infectious disease, and are accordingly of great concern. The clipping procedure may also lead to needle sticks and/or toxic or infectious aerosolization exposure; if the syringe barrel is not also clipped it may be illicitly used once a functional needle is obtained.

SUMMARY OF THE INVENTION

The present invention is directed to a safety syringe having two primary features: the needle is positioned along the side of the barrel, rather than coaxially with the barrel, and the needle is a retractable needle which is irreversibly locked into a safe, post-use, retracted position in a simple and effective manner.

The syringe is of the type having a barrel with a plunger disposed within the bore of the barrel. The syringe includes a needle assembly housed within a needle assembly guide, the needle assembly guide being positioned along the exterior of the syringe barrel. The needle assembly guide provides a path along which the needle assembly moves between an extended position, with the needle exposed, and a retracted position, with the needle encompassed by the needle guide. A flow path exists between the interior of the syringe barrel and the needle assembly when the needle assembly is in the extended position. Additionally, the needle assembly can be locked in the retracted position to prevent syringe reuse.

A primary advantage of the invention is that by providing the needle offset from the axis of the barrel, certain procedures, such as administering fluids intravenously or subcutaneously, is made easier by this radial offset by reducing the angle of incidence between the needle cannula axis and the blood vessel axis or tissue layer plane. Also, radially offset positioning permits the needle to be retracted and extended without interfering with the movement of the plunger, thus making for a simple, compact safety syringe.

Other features and advantages of the invention will appear from the following description in which the preferred embodiment has been set forth in detail in conjunction with the accompanying drawings.

BRIEF DESCRIPTION OF THE DRAWINGS

FIG. 4 shows the syringe of FIG. 3 with the needle assembly in its in-use, extended position and the plunger partially withdrawn from the barrel, thus filling the distal, variable volume region of the barrel with a liquid;

FIG. 5 is a cross-sectional view taken along line 5—5 of FIG. 4;

FIG. 6 is an enlarged view taken along line 6—6 of FIG. 4 showing the flow path fluidly coupling the variable volume region within the barrel with the hollow needle;

DESCRIPTION OF THE PREFERRED EMBODIMENT

Figure 1:
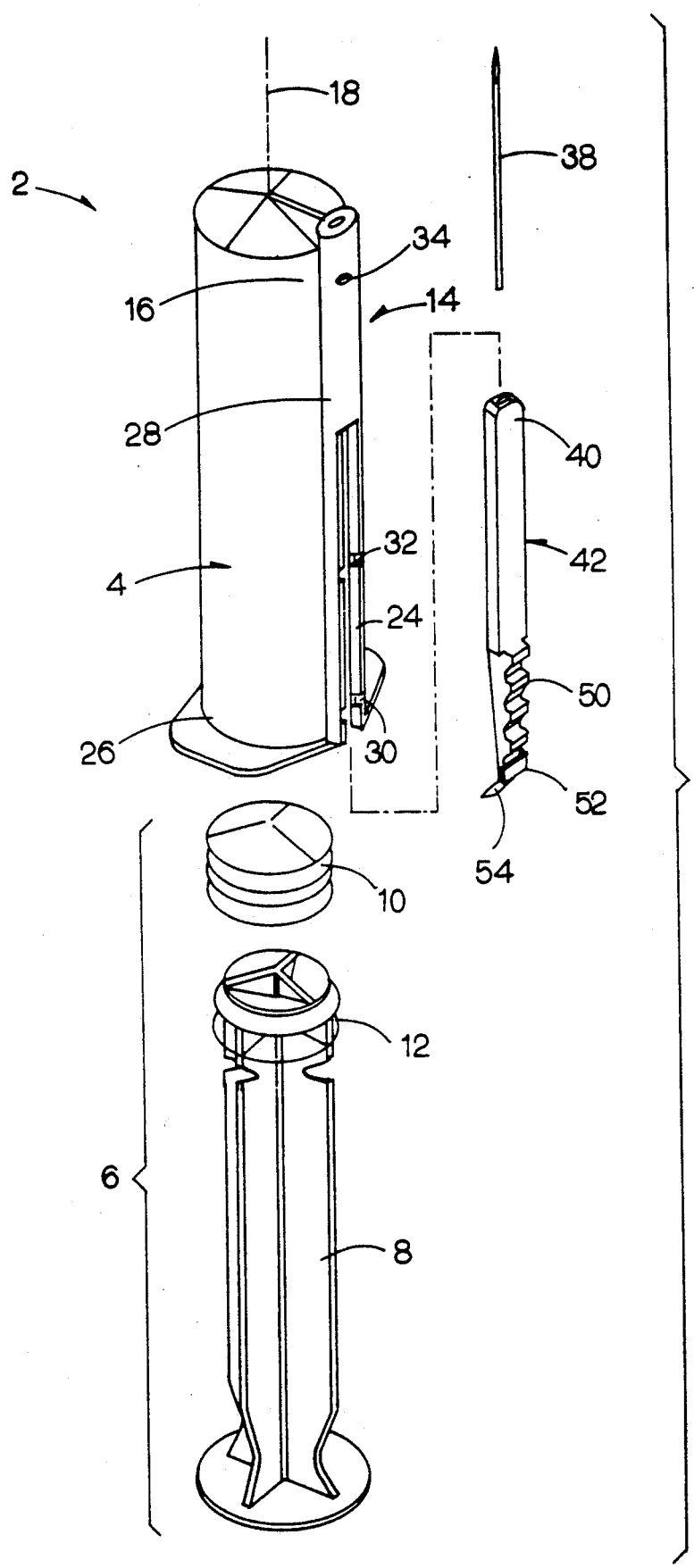
FIG. 1 is an exploded isometric view of a syringe made according to the invention.

FIG. 1 illustrates a syringe 2 including a barrel 4 and a plunger 6. Plunger 6 includes a stem 8 and an elastomeric piston 10 which fits over the head 12 of stem 8. A needle assembly guide 14 is formed as a one-piece molded extension of barrel 4 positioned along the outside or exterior 16 of barrel 4. Barrel 4, guide 14 and stem 8 are preferably clear and made of a medically compatible material, such as polypropylene. Guide 14 is positioned parallel to but radially offset of the axis 18 of barrel 4. Needle assembly guide 14 is seen to be an elongate hollow member having an interior 20 which houses a needle assembly 22. Guide 14 includes a longitudinally extending slot 24 extending from the proximal end 26 of barrel 4 to a position 28 along barrel 4. Slot 24 includes a pair of cutouts 30, 32 configured to temporarily secure needle assembly 22 in the pre-use, retracted position of FIGS. 2 and 3 and the in-use, extended position of FIG. 4 as discussed below. Guide 14 also includes an access opening 34 overlying a port 36 formed in barrel 4; opening 34 permits port 36 to be molded through the wall of barrel 4.

Needle assembly 22 includes a hollow needle 38 mounted to the distal end 40 of a needle mount 42. Needle mount 42 is sized to slide within interior 20 of guide 14. As seen best in FIGS. 5 and 6, needle mount 42 includes an opening 44 which fluidly couples the interior of hollow needle 38 with port 36 when needle assembly 22 is in extended position of FIG. 4. Port 36 and opening 44 creating a flow path from a distal, variable volume region 46 defined within barrel 4 and hollow needle 38. As can be seen best in FIG. 6, the abutting surfaces 47, 48, which surround opening 44 and port 36, have complementary curved shapes to provide a good seal along the flow path formed by port 36 and opening 44.

Figure 3:
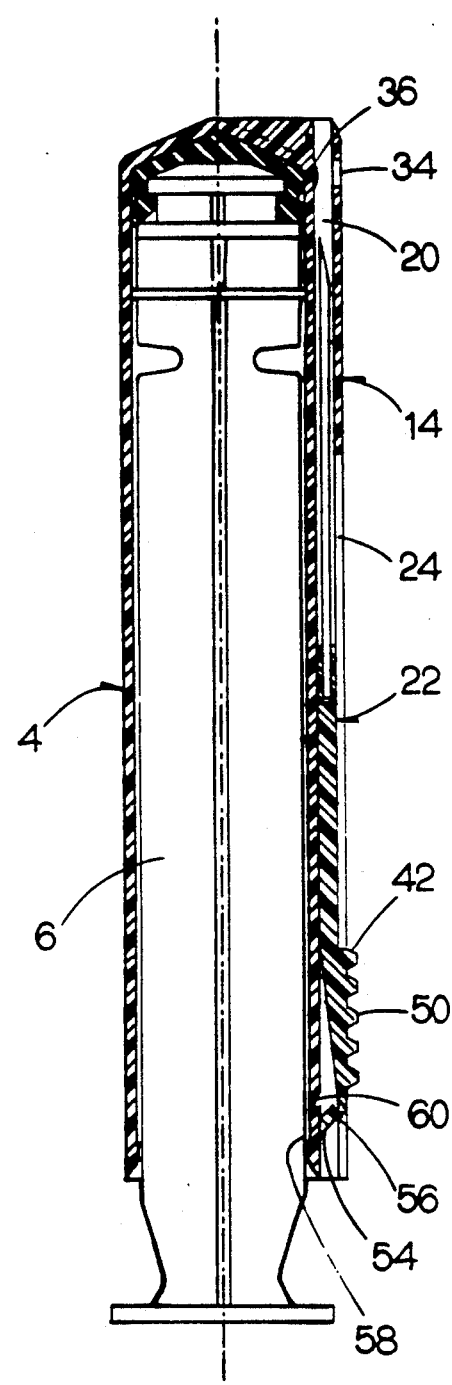
FIG. 3 is a cross-sectional view taken along line 3—3 of FIG. 2.

Needle mount 42 includes a serrated end 50 which extends through slot 24. This allows the user to move needle assembly 22 between the retracted and extended positions of FIGS. 3 and 4. To temporarily secure needle assembly 22 in the retracted and extended positions of FIGS. 3 and 4, serrated end 50 includes an extended width portion 52 sized to engage cutouts 30, 32 when needle assembly 22 is at the retracted and extended positions. As can be seen in FIGS. 3, serrated end 50 is naturally positioned in its radially outward position of FIGS. 3 and 4 so that serrated end 50 must be biased inwardly, that is towards axis 18, to disengage extended width portion 52 from cutouts 30, 32 before needle assembly 22 can be moved along interior 20 of guide 14. This keeps needle assembly 22 from inadvertently moving from its safe, pre-use, retracted position of FIG. 3 or from its in-use, extended, and potentially hazardous, position of FIG. 4.

Figures 7, 8:
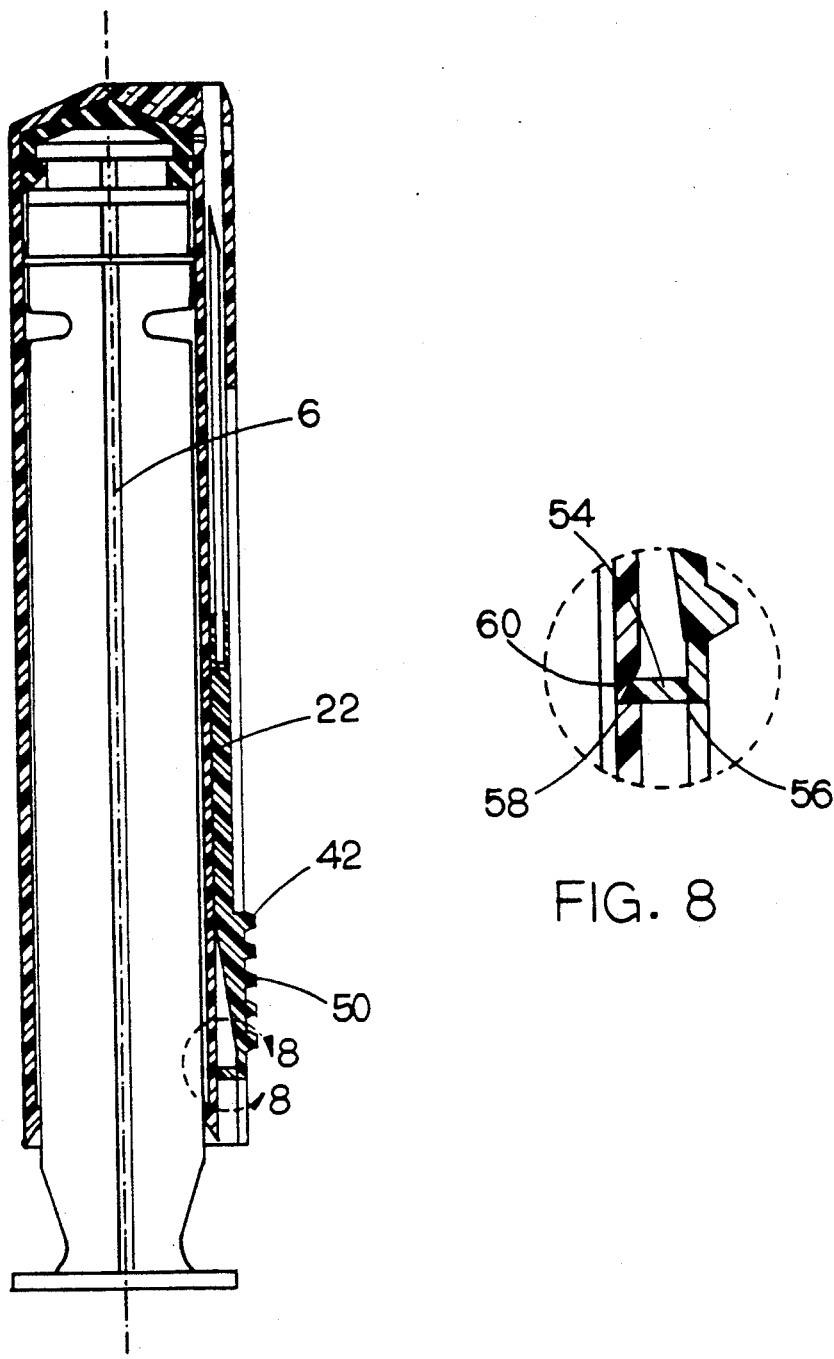
FIG. 7 illustrates the syringe of FIG. 4 after the liquid within the variable volume region has been dispensed through the hollow needle and the needle assembly has been withdrawn to its post-use, locked and retracted position.
FIG. 8 is an enlarged view taken along line 8—8 of FIG. 7 showing the locking tab at one end of the needle mount engaging a recess stop formed in the barrel to prevent radially inward movement of the needle mount, thus locking the needle assembly in the post-use, locked and retracted position.

As can be seen in FIG. 3, needle mount 42 includes a tab 54 extending from extended width portion 52 by a hinge 56. Tab 54 has a bevelled end 58 which, due to its inclination in the pre-use, retracted position of FIG. 3, easily passes over a recess stop 60 formed in barrel 4 directly beneath cutout 30. The normal angular inclination of tab 54 in the pre-use, retracted position permits unimpeded movement of extended width portion 52 inwardly to allow portion 52 to disengage from cutout 30 in the pre-use, retracted position of FIG. 3 as well as from cutout 32 in the in-use, extended position of FIG. 4. However, the configuration and orientation of tab 54 causes the tab to engage recessed stop 60 when moved from the in-use, extended position of FIG. 4 to the post-use, retracted and irreversibly locked position of FIG. 7. This locking is illustrated best in FIG. 8. As can be seen, radially inward movement of extended width portion 52 is prevented by the engagement of tab 54 within recessed stop 60. This prevents the disengagement of extended width portion 52 from cut-out 30, thus irreversibly locking needle assembly 22 in the retracted position of FIG. 7. Syringe 2 is thus deactivated for safe, post-use disposal.

Figure 2:
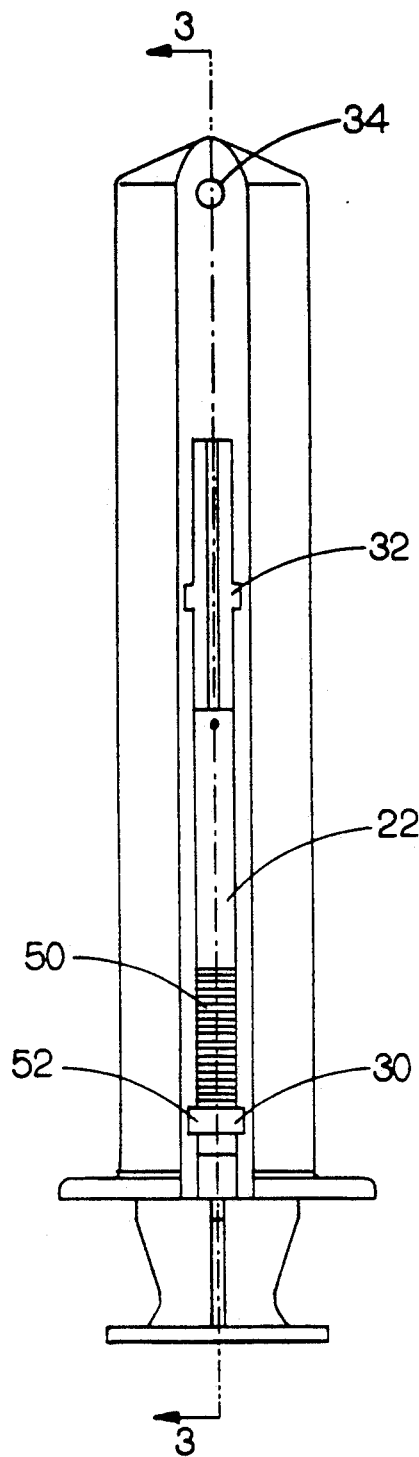
FIG. 2 is a front elevational view thereof with the plunger fully inserted into the barrel and the needle assembly in its pre-use, retracted position.

Syringe 2 is preferably provided in the pre-use, retracted position of FIGS. 2 and 3 in some sort of sterile packaging or wrapping. Just prior to use, syringe 2 is removed from the packaging or wrapping and needle assembly 22 is moved from the position of FIGS. 2 and 3 to the position of FIG. 4 by pressing on serrated end 50 to disengage extended width portion 52 from cutout 30. Serrated end 50 reaches the end of slot 24. Releasing serrated end 50 permits portion 52 to engage cutout 32 to temporarily lock needle assembly 20 in the extended position of FIG. 4. The tip of needle 38 is then inserted into a liquid 62 to be injected and plunger 6 is partially retracted as shown in FIG. 4 to draw liquid 62 into region 46 as illustrated in FIG. 4. The injection is then given in the normal manner, with liquid 62 passing through the flow path defined by port 36 and opening 44 and finally through needle 38. After the injection has been completed, the user presses on serrated end 50 to disengage portion 52 from cutout 32 and then draws needle assembly 22 to the post-use, retracted and irreversibly locked position of FIG. 7. In doing so, tab 54 engages recessed stop 60, thus forcing portion 52 into cutout 30 to irreversibly lock needle assembly 22 in the safe, post-use, retracted and locked position.

Modification and variation can be made to disclosed embodiments without departing from the subject of the invention as defined in the following claims. For example, the needle assembly and needle assembly guide could be modified to be a removable assembly for mounting to a conventional syringe structure having a conventional twist lock tip. The invention could also be practiced using packaged pharmaceutical containers of the type having a septum at one end and a piston at the other. A protective sheath may be used to cover needle 38 and temporarily seal port 36.

What is claimed is:

1. A syringe structure of the type with a barrel having a bore with a plunger slidably mounted therein, the improvement comprising:
   a hollow needle;
   a means for mounting the needle at the outside of the barrel for movement along a path, parallel to but radially offset from the axis of the bore, between an extended position, at which at least a portion of the needle is exposed, and a retracted position, at which the needle is enclosed within the mounting means;
   the mounting means including a deflectable member removably securing the needle assembly in the extended and retracted positions;
   means for preventing the deflection of the deflectable member when the needle moves to the retracted position from the extended position so to irreversibly lock the needle in the retracted position; and
   means for fluidly coupling the barrel bore with the needle bore when the needle is in the extended position.

2. A syringe structure comprising:

a barrel having an interior, an exterior, an open proximal end and a distal end;

a plunger slidably mounted within the interior of the barrel, and extending from the proximal end;

a needle assembly including a hollow needle and a movable needle mount portion, the needle having a central bore;

a needle assembly guide secured directly to the exterior of the barrel, and having a needle assembly path along which the needle assembly can move between an extended position, with the needle exposed, and a retracted position, with the needle housed within the needle assembly guide;

said needle assembly guide including first and second catches configured to engage the movable portion of the needle mount when the needle assembly is at the extended and retracted positions to temporarily secure the needle assembly at said positions;

means for irreversibly locking the needle assembly in the retracted position including a tab extending from the movable portion and means for engaging the tab as the needle assembly is moved in a direction from the extended position to the retracted position to keep the movable portion engaged with the second catch thus irreversibly locking the needle assembly at the retracted position; and means forming a flow path for fluidly coupling the interior of the barrel at the distal end to the central bore of the hollow needle when the needle assembly is in the extended position.

3. A syringe structure comprising:

a barrel having an interior, an exterior, an open proximal end and a distal end;

a plunger slidably mounted within the interior of the barrel, and extending from the proximal end;

a needle assembly including a hollow needle and a needle mount, the needle having a central bore and the needle mount including a rearward portion which is radially deflectable from a natural radially outward position to a position against the exterior of said barrel;

an extended width portion on said rearward portion;

a needle assembly guide integral with the exterior of the barrel, and having a needle assembly path along which the needle assembly can move between an extended position, with the needle exposed, and a retracted position, with the needle housed within the needle assembly guide;

a flow path, formed by the barrel and the needle assembly, fluidly coupling the interior of the barrel at the distal end to the central bore of the hollow needle when the needle assembly is in the extended position;

the needle assembly guide including first and second catches configured to engage the extended width portion of the rearward portion of the needle mount when the needle assembly is at the extended and retracted positions and the rearward portion of the needle mount is in its naturally radially outward position to temporarily secure the needle assembly at said positions; and a rearwardly extending tab secured to the rearward portion of the needle mount and means on the exterior of said barrel for engaging the tab as the needle assembly is moved in a direction from the extending position to the retracted position to keep the extended width portion engaged with the second catch thus irreversibly locking the needle assembly at the retracted position.

* * * * *